(12) United States Patent
Ogasawara

(10) Patent No.: US 10,829,809 B2
(45) Date of Patent: Nov. 10, 2020

(54) GENE-SPECIFIC UNBIASED AMPLIFICATION METHOD

(71) Applicant: TOHOKU UNIVERSITY, Sendai (JP)

(72) Inventor: Koetsu Ogasawara, Sendai (JP)

(73) Assignee: TOHOKU UNIVERSITY, Sendai (JP)

( * ) Notice: Subject to any disclaimer, the term of this patent is extended or adjusted under 35 U.S.C. 154(b) by 31 days.

(21) Appl. No.: 15/552,971

(22) PCT Filed: Feb. 23, 2016

(86) PCT No.: PCT/JP2016/055192
§ 371 (c)(1),
(2) Date: Aug. 23, 2017

(87) PCT Pub. No.: WO2016/136716
PCT Pub. Date: Sep. 1, 2016

(65) Prior Publication Data
US 2018/0245130 A1    Aug. 30, 2018

(30) Foreign Application Priority Data

Feb. 23, 2015  (JP) .................................. 2015-033236

(51) Int. Cl.
| | | |
|---|---|---|
| *C12Q 1/686* | (2018.01) | |
| *C12Q 1/6806* | (2018.01) | |
| *C12Q 1/6855* | (2018.01) | |
| *C12N 15/11* | (2006.01) | |

(52) U.S. Cl.
CPC .............. *C12Q 1/686* (2013.01); *C12N 15/11* (2013.01); *C12Q 1/6806* (2013.01); *C12Q 1/6855* (2013.01)

(58) Field of Classification Search
None
See application file for complete search history.

(56) References Cited

U.S. PATENT DOCUMENTS

| | | | | |
|---|---|---|---|---|
| 6,197,557 B1 * | 3/2001 | Makarov | .............. | C12Q 1/6855 435/6.1 |
| 6,509,157 B1 * | 1/2003 | Martinez | .............. | C12Q 1/6848 435/6.12 |
| 2012/0316074 A1 * | 12/2012 | Saxonov | ................ | C12N 15/10 506/2 |
| 2014/0303000 A1 * | 10/2014 | Armour | ............. | C12N 15/1093 506/2 |
| 2016/0032357 A1 * | 2/2016 | Barany | ................ | C12Q 1/6858 435/6.11 |

FOREIGN PATENT DOCUMENTS

| | | |
|---|---|---|
| WO | 2013059746 A1 | 4/2013 |
| WO | 2013191775 A2 | 12/2013 |

OTHER PUBLICATIONS

Haas et al. Journal of Clinical Microbiology 1993; 31: 1293-1298 (Year: 1993).*
Muha et al. PLoS Genetics 2012 8: 31002738. (Year: 2012).*
Fadda and Pomes. Nucleic Acids Research 2011; 39: 767-780. (Year: 2011).*
Chen et al. Scandinavian Journal of Immunology 1992; 35: 539-549. (Year: 1992).*
Zhang et al. Dye-Free Gene Expression Detection by Sequence-Tagged Reverse-Transcription Polymerase Chain Reaction Coupled with Pyrosequencing. Analytical Chemistry 2009; 81: 273-281 . . . (Year: 2009).*
Kobayashi H. et al., Characterization of T Cell Receptors of Th1 Cells Infiltrating Inflamed Skin of a Novel Murine Model of Palladium-Induced Metal Allergy, PLos One, Oct. 3, 2013, vol. 8 Issue 10, e76385.

* cited by examiner

*Primary Examiner* — Angela M. Bertagna
(74) *Attorney, Agent, or Firm* — Lucas & Mercanti, LLP

(57) ABSTRACT

The present invention is intended to provide a method of amplifying a target gene without bias and an adapter DNA use therefor. The adapter DNA of the present invention is double-stranded adapter DNA, which is used for unbiased gene amplification.

3 Claims, 10 Drawing Sheets

Specification includes a Sequence Listing.

Fig. 9
A
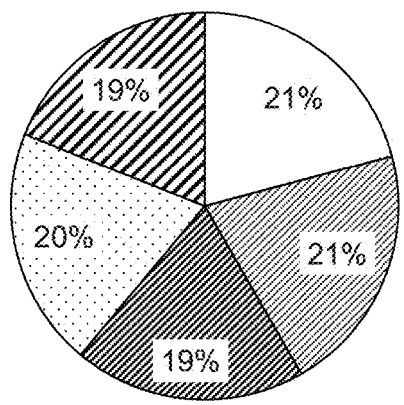
B
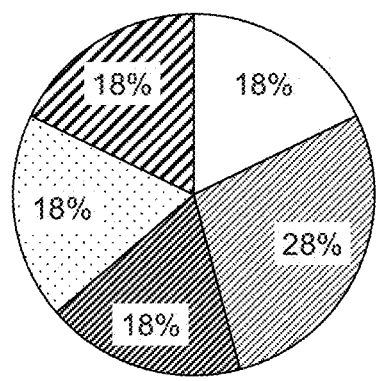

■ TCR gene amplification by conventional AL-PCR (old adapter)
□ TCR gene amplification by unbiased gene amplification (new adapter)

GENE-SPECIFIC UNBIASED AMPLIFICATION METHOD

CROSS-REFERENCE TO RELATED APPLICATIONS

This application is a 371 of PCT/JP2016/055192, filed Feb. 23, 2016, which claims the benefit of Japanese Patent Application No. 2015-033236, filed Feb. 23, 2015.

TECHNICAL FIELD

The present invention relates to a method of specific unbiased amplification of a target gene and an adapter used therefor.

BACKGROUND ART

Hitherto, PCR methods have been used as methods of amplifying particular genes. In addition, in the case of unbiased amplification for uniform amplification, an adapter is provided, and gene amplification has been conducted using primers that are a partial adapter sequence and a gene-specific sequence, respectively. However, since the provided adapter is added to both ends of DNA, the adapter portion alone induces PCR amplification, which has been problematic. Although it has been considered possible to solve such problem via digestion with a restriction enzyme, it has been technically problematic.

Conventional techniques are intended to carry out amplification of a specific gene without bias by inserting a restriction enzyme site into an adapter portion or a cDNA end (3' end side) and carrying out restriction enzyme treatment. However, restriction enzyme treatment cannot be achieved with 100% certainty, and PCR amplification takes place only at the adapter portion due to untreated DNA or the remaining adapter, which has been problematic.

CITATION LIST

Non-Patent Literature

Non-Patent Literature 1: Kobayashi H. et al., PLoS One 8: e76385 doi: 10.1371/journal.pone.0076385.

SUMMARY OF INVENTION

Technical Problem

An object of the present invention is to provide a method of amplifying a target gene without bias and an adapter used therefor.

Solution to Problem

Providing an adapter is essential for an unbiased gene amplification method. However, since the provided adapter is added to both ends of DNA, the adapter portion alone induces PCR amplification, which has been problematic. Although it has been considered possible to solve such problem via digestion with a restriction enzyme, it has been technically problematic.

The present inventors found that it is possible to prevent an adapter portion alone from inducing PCR amplification by providing uracil that is not present in usual DNA to the adapter portion and digesting uracil with DNA glycosylase so as to remove a part (sense or antisense DNA strand) of the adapter portion without restriction enzyme treatment. This has led to the completion of the present invention. According to the gene-specific unbiased amplification method of the present invention, it becomes possible to amplify a specific gene without bias.

Specifically, the present invention is described as below.

[1] Double-stranded adapter DNA, which is used for unbiased gene amplification and has the following features:
(a) the double-stranded adapter DNA has a sense strand and an antisense strand that are annealed with each other, the base length of the sense strand being equal to or longer than the base length of the antisense strand;
(b) the base length of the sense strand is 15 to 40 bp;
(c) the antisense strand includes a plurality of uracil bases, each uracil is removed by treating an adapter portion with uracil DNA glycosylase (UNG), and then, heat treatment is performed to degrade the antisense strand;
(d) at least one end of the adapter DNA is in the form of a blunt end;
(e) the other end of the adapter DNA binds to a target gene to be amplified; and
(f) a part or all of the sense strand corresponds to a forward primer sequence used for gene amplification.

[2] The double-stranded adapter DNA according to [1], wherein the number of uracil bases included in the antisense strand accounts for 10% to 25% of the number of bases of the antisense strand, and uracil is present every 5 to 10 bases.

[3] The double-stranded adapter DNA according to [1] or [2], wherein a phosphate group is bound to the 5' end of the antisense strand and an amino group is bound to the 3' end thereof.

[4] An unbiased gene amplification kit, which includes the adapter DNA according to any one of [1] to [3] and a primer comprising a part or all of a sequence of the sense strand of the adapter DNA.

[5] An inhibitory primer, which is used for unbiased gene amplification by inhibiting gene amplification induced with a forward primer alone in an adapter ligation PCR amplification method in which a double-stranded adapter DNA and a forward primer comprising a partial sequence of a sense strand of the double-stranded adapter DNA are used, wherein
(a) the inhibitory primer has a sequence comprising:
(i) all or a part of a sequence of an anchor sequence portion of an anchored oligo dT primer in which an anchor sequence is ligated to the 5' end of an oligo dT primer, the anchored oligo dT primer being used when synthesizing single-stranded cDNA from mRNA of a target gene to be amplified; or
(ii) a partial sequence of a sense strand of a double-stranded adapter used in an adapter ligation PCR amplification method, which is a sequence present on the 3' end side of the sequence of the forward primer, and
(b) the inhibitory primer is modified with a phosphate group, an amino group, or dideoxyl NTP on its 3' end side.

[6] An unbiased gene amplification kit, which includes the adapter DNA according to any one of [1] to [3], a primer comprising a part or all of a sequence of the sense strand of the adapter DNA, and the inhibitory primer according to [5].

[7] A method of amplifying a target gene without bias in one direction by PCR, comprising the following steps of:
(i) ligating the double-stranded adapter DNA according to any one of [1] to [4] to both ends of double-stranded cDNA;
(ii) treating a gene ligated to the double-stranded adapter DNA with uracil DNA glycosylase (UNG) and further conducting heat treatment, thereby degrading the antisense strand of the adapter DNA; and (iii) conducting PCR amplification using a forward primer comprising a part or all of a sequence of a sense strand of the double-stranded adapter DNA and a reverse primer that is specifically annealed with a target gene.

[8] The method of amplifying a target gene without bias in one direction by PCR according to [7], wherein the reverse primer induces an elongation reaction while the forward primer alone does not induce an elongation reaction, and after a complementary strand of the sense strand of the adapter is formed, the forward primer is annealed with the complementary strand so that an elongation reaction is induced, indicating that elongation induced by the reverse primer and elongation induced by the forward primer take place in the above order in one direction.

[9] The method of amplifying a target gene without bias in one direction by PCR according to [7] or [8], wherein the inhibitory primer according to [5] is further used so that an elongation reaction induced by the forward primer alone is inhibited.

[10] A method of analyzing a TCR or BCR repertoire, which comprises synthesizing cDNA from total RNA extracted from T cells or B cells, conducting comprehensive amplification of a TCR gene or BCR gene repertoire using, as a reverse primer, a primer that is specifically annealed with a C region sequence of a T cell receptor (TCR) or B cell receptor (BCR) by the method according to [7] or [8], and conducting sequencing using a sequencer.

This specification includes part or all of the contents as disclosed in the specification and/or drawings of Japanese Patent Application No. 2015-033236, which is a priority document of the present application.

Advantageous Effects of Invention

According to the gene amplification method of the present invention, in which an adapter including uracil is used for adapter ligation PCR, it has become possible to amplify a specific gene without bias. The gene amplification method of the present invention makes it possible to conduct comprehensive amplification of various repertoires of T cell receptors (TCRs) and B cell receptors (BCRs) and to carry out repertoire analysis of TCRs or BCRs by sequencing using a next-generation sequencer. It can be said that the present method is an unbiased gene amplification method, characterized in that it is superior to conventional adapter ligation PCR (AL-PCR) methods in all aspects and also superior to any available method.

BRIEF DESCRIPTION OF DRAWINGS

FIG. 1A illustrates that a double strand comprising a 5'-end-side long strand (sense strand) and a 3'-end-side short strand (antisense strand) present at both ends of a gene corresponds to an adapter, symbol "×" on a short strand indicates degradation of the short strand via UNG treatment and heat treatment. FIG. 1B illustrates that after an antisense strand is degraded, amplification is induced by a target gene-specific reverse primer in a direction shown with arrow 1, and after elongation proceeds to a strand complementary to the sense strand of the adapter, amplification is induced by a forward primer that binds to the adapter in a direction shown with arrow 2.

FIG. 2A illustrates a case in which no inhibitory primer is used and FIG. 2B illustrates a case in which an inhibitory primer is used.

FIG. 6A shows the results of the amplification using the forward primer (TO993) and the reverse primer (MCA195) and the results of the amplification using the forward primer (TO993) alone. FIG. 6B shows the results of the amplification using the inhibitory primer (T0979).

FIG. 8A indicates the results for a case in which mouse TCRs having five different sizes were uniformly mixed. FIG. 8B indicates the results of the conventional amplification method with the addition of the old-type adapter. FIG. 8C indicates the results of the amplification method of the present invention with the addition of the new-type adapter.

FIG. 9 shows abundance of five mouse TCRs having different sizes before and after PCR. FIG. 9A shows abundance rate of each TCR in a uniform mixture of mouse TCRs having five different sizes before PCR. FIG. 9B shows abundance rate of each TCR after PCR with the use of the adapter of the present invention.

DESCRIPTION OF EMBODIMENTS

Figure 1:
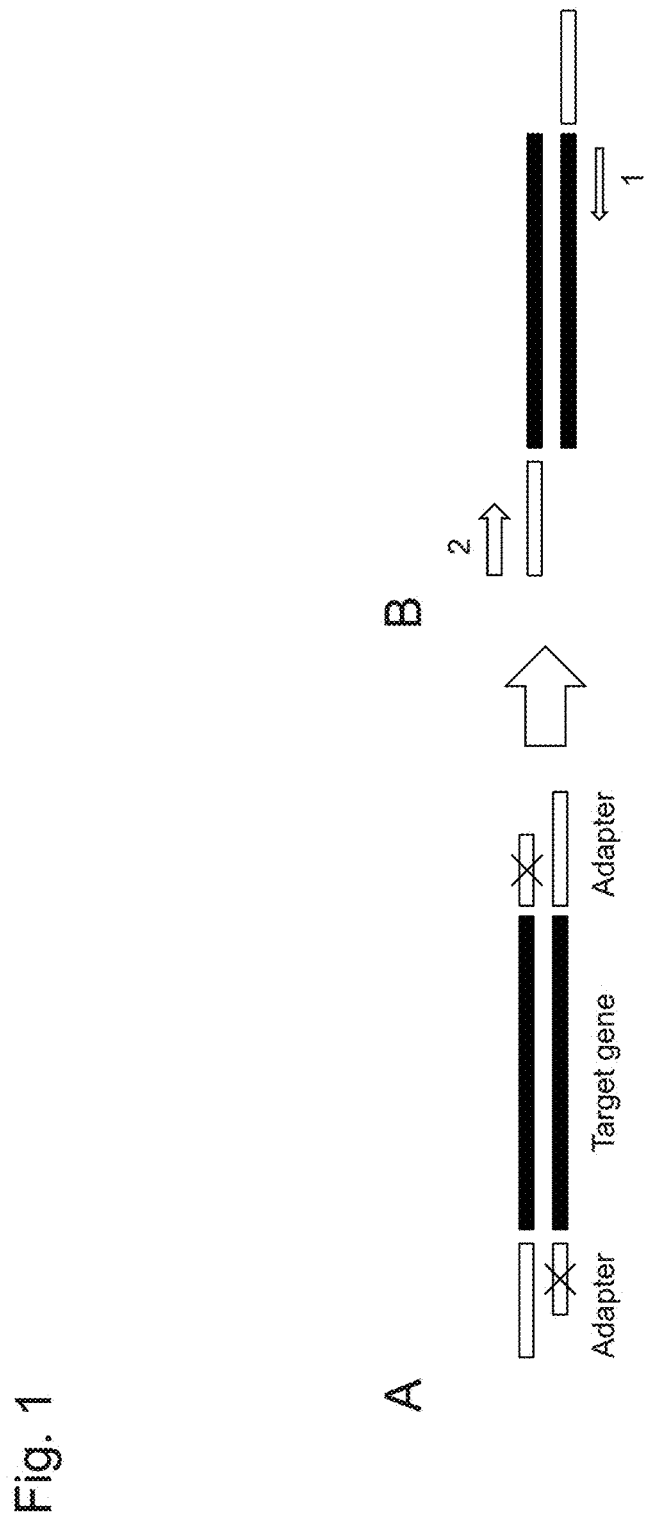
FIG. 1 shows the principle of the gene amplification method of the present invention and the positional relationship of a target gene, an adapter, and a primer.

Hereinafter, the present invention is described in detail.

The present invention concerns a method of amplifying a target gene to be amplified without bias, which is an adapter ligation PCR amplification method using an unbiased gene amplification adapter having a particular sequence. According to the gene amplification method of the present invention, the above adapter is used without conducting restriction enzyme treatment by inserting a restriction enzyme site to an adapter portion or cDNA 3' end, thereby preventing PCR amplification from taking place at the adapter portion alone so that PCR amplification proceeds only in one direction. When PCR proceeds in one direction, it is also referred to as PCR polarity.

In addition, the present invention encompasses a method of amplifying a particular gene without bias using an inhibitory primer.

1. Adapter

The adapter of the present invention comprises a sense strand and an antisense strand, which are annealed with each other to form double-stranded DNA. In the present invention, the term "adapter" also refers to "adapter DNA." One strand of the adapter includes uracil (dUTP: deoxyuridine triphosphate) at a constant frequency. An adapter having an antisense strand including uracil is explained below. In the following explanation, a sense strand and an antisense strand are interchangeable. In a sense strand portion complementary to an antisense strand, a base corresponding to uracil in the antisense strand is adenine. The base length of the sense strand and that of the antisense strand may be the same. The antisense strand including uracil may be shorter than the sense strand. At least one end of the adapter is in the form of a blunt end. In a case in which the antisense strand is shorter than the sense strand, one end of the adapter is in the form of a blunt end and the other end thereof is in the form of a protruding end so that when the adapter is used, its blunt end is ligated to a target gene to be amplified. In a case in which the base length of the sense strand and that of the antisense strand are the same, each of both ends of the adapter is in the form of a blunt end.

In a gene amplification method using the adapter of the present invention, a primer comprising a sequence included in a sense strand of the adapter is used as a forward primer. Thus, in order to prevent the forward primer from being annealed with a non-adapter portion, an adapter sequence is determined to be an artificial sequence that is not present or hardly present in the genome of an organism as a subject of gene amplification. Alternatively, the nucleotide sequence of the adapter is determined to be a sequence that is not present in a target family gene to be amplified. For example, in a case in which gene amplification is conducted for T cell receptor or B cell receptor repertoire analysis, the nucleotide sequence is determined to be a sequence that is not present in T cell receptors or B cell receptors. As a result, unless the adapter is ligated to an end of a target gene, a primer comprising a sequence included in the sense strand of the adapter does not induce amplification.

The base length of the adapter is 15 to 40 bases, preferably 20 to 35 bases, and further preferably 20 to 30 bases. In a case in which the base length of a sense strand and that of an antisense strand are different, the base strength of an antisense strand serving as a short strand is 10 to 20 bases and preferably 10 to 15 bases.

Uracil included in an antisense strand is allowed to be present in such a manner that uracil is removed by uracil DNA glycosylase (UNG) to generate an abasic site and then each abasic site is degraded via heat treatment, thereby degrading the entire antisense strand. For example, the number of bases that may be uracil accounts for 10% to 50%, preferably 10% to 25%, and further preferably 10% to 20% or 12% to 20% of the total number of bases of the antisense strand of the adopter. Uracil does not necessarily regularly appear in the antisense strand. However, the antisense strand is designed so that uracil appears, for example, every 3 to 15 bases, preferably every 3 to 10 bases, and further preferably every 5 bases. In order to eventually degrade an antisense strand by means of uracil DNA glycosylase and heat treatment, it is preferable that uracil be present evenly across the antisense strand without bias.

In addition, the adapter sequence is designed so that it has a GC content of approximately 50%, i.e., 40% to 60%, and preferably 45% to 55%. Further, it is preferable that no sequence comprising consecutive bases is present. Note that, in a case in which an adapter portion is allowed to include a restriction enzyme site, adenine (A) might appear consecutively in the sense strand. In such case, the antisense strand may partially include 2 to 3 uracil bases in a consecutive manner, which is acceptable in this case.

A phosphate group is bound to the 5' end of the antisense strand on the blunt end side in order to ligate the antisense strand to a target gene. In other words, the 5' end of the antisense strand, which is an end capable of binding to a target gene (binding side end), is phosphorylated. By phosphorylating only one end in such manner, even in a case in which both ends of an adapter are each in the form of a blunt end, the adapter cannot be ligated to a target gene via the opposite end to the phosphorylate end. In addition, in a case in which one end of the adapter is in the form of a blunt end and the other end thereof is in the form of a protruding end, the adapter is ligated to a target gene only on the blunt end side.

It is preferable that a modifying group capable of inhibiting PCR elongation reaction, such as an amino group, is ligated to the 3' end of an antisense strand. As stated below, an antisense strand includes uracil so that the antisense strand is degraded via uracil DNA glycosylase (UNG) treatment and heating. Therefore, a primer is not bound to an adapter portion, which does not induce elongation reaction. However, in consideration of a case in which an antisense strand is not degraded, it is preferable that a modifying group capable of inhibiting PCR elongation reaction, such as an amino group, is ligated to the antisense strand. As a result of ligation of an amino group, an antisense strand does not serve as a primer, which does not induce elongation reaction.

The adapter is ligated to a gene, followed by treatment with uracil DNA glycosylase (UNG). Thus, each uracil-glycoside bond is degraded, thereby removing uracil. As a result, alkali-sensitive abasic sites are generated in antisense strand DNA of the adapter. Thereafter, heat treatment is conducted at 80° C. to 90° C. for several minutes. Thus, each abasic site from which uracil has been removed is degraded, and the antisense strand of the adapter is completely degraded.

According to the PCR gene amplification method of the present invention, an adapter forward primer that is annealed to an adapter portion is designed with all or a part of the sense strand sequence of an adapter. It is a sequence comprising preferably 10 to 30 bases and more preferably 15 to 25 bases from the 5' end of the sense strand.

The adapter of the present invention can be produced by synthesizing and annealing a sense strand and an antisense strand by publicly known methods. An antisense strand including uracil can be synthesized using dUTP.

Examples of adapters comprising the following sequences can be described as the adapter of the present invention.

(1) Adapter obtained by annealing a sense strand consisting of the nucleotide sequence of SEQ ID NO: 2 with an antisense strand consisting of the nucleotide sequence of SEQ ID NO: 3, which has a phosphorylated 5' end. An amino group may be bound to the 3' end of the antisense strand. In the case of this adapter, one end bound to a phosphate group is in the form of a blunt end and the other end is in the form of a protruding end. When such adapter is used, a primer comprising the nucleotide sequence of SEQ ID NO: 4 is used as a forward primer.

(2) An adapter obtained by annealing a sense strand consisting of the nucleotide sequence of SEQ ID NO: 8 with an antisense strand consisting of the nucleotide sequence of SEQ ID NO: 9, which has a phosphorylated 5' end. An amino group may be bound to the 3' end of the antisense strand. In the case of this adapter, both ends are each in the form of a blunt end. When such adapter is used, a primer comprising the nucleotide sequence of SEQ ID NO: 17 is used as a forward primer.

(3) An adapter obtained by annealing a sense strand consisting of the nucleotide sequence of SEQ ID NO: 8 with an antisense strand consisting of the nucleotide sequence of SEQ ID NO: 10, which has a phosphorylated 5' end. An amino group may be bound to the 3' end of the antisense strand. In the case of this adapter, both ends are each in the form of a blunt end. When such adapter is used, a primer comprising the nucleotide sequence of SEQ ID NO: 17 is used as a forward primer.

(4) An adapter obtained by annealing a sense strand consisting of the nucleotide sequence of SEQ ID NO: 8 and an antisense strand consisting of the nucleotide sequence of SEQ ID NO: 11, which has a phosphorylated 5' end. An amino group may be bound to the 3' end of the antisense strand. In the case of this adapter, both ends are each in the form of a blunt end. When such adapter is used, a primer comprising the nucleotide sequence of SEQ ID NO: 17 is used as a forward primer.

The present invention also encompasses an unbiased gene amplification kit, which comprises the above adapter and a primer consisting of a par or all of the sense strand sequence of the adapter. In addition to the above, the kit may comprise a reverse primer that is specific to a target gene, DNA polymerase, deoxyribonucleotide, and the like. It may further include an inhibitory primer specified in 4 below.

2. Gene Amplification Method of the Present Invention

According to the gene amplification method of the present invention, an adapter forward primer comprising all or a part of the sense strand sequence of the above adapter and having an endogenous sequence in the sense strand of the adapter is used as a forward primer, and a primer that is annealed in the vicinity of the 3' end of a target gene to be amplified is used as a reverse primer.

A target gene according to the gene amplification method of the present invention is not limited, and it may be any genomic DNA. At first, total mRNA is extracted and purified from cells to synthesize single-stranded cDNA. cDNA can be synthesized by a publicly known method using a synthesis primer specific to a gene of interest and a reverse transcription enzyme. In addition, an oligo dT primer or an anchored oligo dT primer to which an anchor sequence is ligated may be used. Here, the anchor sequence of an anchored oligo dT primer is a sequence that is ligated on the 5' end side of an oligo dT sequence and is not complementary to a target gene sequence. For example, it includes a restriction enzyme site. It may also include a sequence of an inhibitory primer specified in 4 below. The base length of an anchor sequence is not limited, but it may be 10 to 40 bases. DNA that is complementary to synthesized single-stranded cDNA is synthesized to synthesize double-stranded cDNA. Species of an organism as the origin of cells is not limited. However, cells to be used are preferably eukaryotic cells, more preferably mammalian cells, and particularly preferably human or murine cells. A series of cDNAs synthesis can be performed using a commercially available cDNA synthesis kit. Upon binding of an adapter (ligation), it is necessary to allow DNA as the origin, for example, synthesized cDNA or genomic DNA, to have a blunt end.

The adapter of the present invention is ligated to both ends of synthesized double-stranded cDNA using DNA ligase. Examples of DNA ligase that can be used include mesophilic DNA ligases such as T4 DNA ligase and *E. coli* DNA ligase. In addition, thermostable DNA ligase may be used.

Next, a gene ligated to the adapter is treated with uracil DNA glycosylase (UNG). Treatment can be conducted at 20° C. to 30° C. for 5 to 30 minutes. As a result of treatment with uracil DNA glycosylase (UNG), each uracil glycoside bond is degraded, and thus, uracil is removed. Accordingly, alkali-sensitive abasic sites are generated in antisense strand DNA of the adapter. Thereafter, heat treatment is conducted at 80° C. to 100° C., for example, 95° C. for several minutes, for example, 2 minutes. Thus, each abasic site, from which uracil has been removed, is degraded, and thus, the antisense strand of the adapter is completely degraded. Further, an antisense strand of the excessively existing adapter can also be degraded. In a case in which an adapter excessively exists, the antisense strand of a free adapter serves as a primer, which might induce unintended amplification. By degrading the antisense strand of a free adapter, it is possible to avoid unintended amplification. As a result, only the sense strand of the adapter is allowed to remain. It is preferable to use temperature-sensitive uracil DNA glycosylase (UNG). It is possible to inactivate an enzyme itself via heat treatment using a temperature-sensitive enzyme.

PCR elongation reaction is carried out by adding an adapter forward primer that is a forward primer consisting of all or a part of the sense strand sequence of an adapter and a reverse primer that is complementary to a partial sequence of a target gene and specific to the target gene. An adapter forward primer is designed with all or a part of the sense strand sequence of an adapter. It comprises preferably 10 to 30 bases and more preferably 15 to 25 bases from the 5' end of a sense strand. In addition, an adapter primer is annealed with an adapter antisense strand that is a strand complementary to an adapter sense strand. In view of this, it may have one to several and preferably one or two mismatches with respect to the antisense strand sequence, and it only needs to have a sequence that can be hybridized with the antisense strand under stringent conditions. A reverse primer comprises a nucleotide sequence complementary to a sequence located in the vicinity of the 3' end of a target gene, and it is a sequence comprising 10 to 30 bases and preferably 15 to 25 bases. In addition, it may have one to several and preferably one or two mismatches with respect to the nucleotide sequence of a target gene, and it only needs to have a sequence that can be hybridized with the target gene under stringent conditions. PCR elongation reaction can be conducted by a publicly known method using DNA polymerase under generally used conditions. For example, it can be conducted by repeating about 30 cycles of heating at 98° C. for 10 seconds, cooling at 60° C. for 30 seconds, and heating at 68° C. for 60 seconds.

Upon PCR amplification reaction, as the antisense strand of the adapter is degraded, the forward primer is not annealed with the antisense strand. Therefore, the forward primer does not induce an amplification reaction at the beginning. Meanwhile, the reverse primer is annealed in the vicinity of the 3' end of the sense strand of a target gene, thereby allowing an amplification reaction to proceed. The reverse primer allows DNA synthesis to proceed so that elongation proceeds to a complementary strand portion of a sense strand of the adapter portion, resulting in formation of a complementary strand. This allows the forward primer to be annealed with a complementary strand portion of an antisense strand of the adapter. As a result, the forward primer allows amplification to proceed. In other words, unless an antisense strand of the adapter is generated through gene elongation, the forward primer is not annealed with the adapter, thereby preventing the forward primer alone from inducing amplification. Alternatively, according to the method of the present invention, the forward primer alone does not induce amplification. Thus, the forward primer is annealed with DNA formed as a result of elongation induced by the reverse primer, which may only allow the forward primer and the reverse primer to induce amplification.

In fact, since amplification induced by an adapter primer takes place after amplification induced by a target gene-specific primer according to the gene amplification method of the present invention, elongation induced by the reverse primer and elongation induced by the forward primer take place in such order in one direction, thereby always allowing gene amplification to proceed in one direction. According to the present invention, the expression "amplification in one direction" means this amplification.

According to the gene amplification method of the present invention, gene amplification can be carried out without bias while maintaining the abundance rate of each mRNA in cells. FIG. 1 illustrates the principle of the gene amplification method of the present invention (a double strand shown in black at the center) and the positional relationship of and a target gene, an adapter, and a primer. FIG. 1A illustrates that a double strand comprising a 5'-end-side long strand (sense strand) and a 3'-end-side short strand (antisense strand) present at both ends of a gene corresponds to an adapter, symbol "×" on a short strand indicates degradation of the short strand via UNG treatment and heat treatment. FIG. 1B illustrates that after an antisense strand is degraded, amplification is induced by a target gene-specific reverse primer in a direction shown with arrow 1, and after elongation proceeds to a strand complementary to the sense strand of the adapter, amplification is induced by a forward primer that binds to the adapter in a direction shown with arrow 2.

3. T Cell Receptor and B Cell Receptor Repertoire Analysis According to the Gene Amplification Method of the Present Invention According to the gene amplification method of the present invention, it is possible to analyze a repertoire of antigen receptors such as a T cell receptor (TCR) or a B cell receptor (BCR) without bias.

A T cell receptor and a B cell receptor are generated via somatic gene recombination of gene regions (segments). There exist gene regions, which are a V (variable) region, a D (diversity) region, a J (joining) region, and a C (constant) region. T cell receptor and B cell receptor repertoires expand through recombination (reconstruction) known as V(D)J recombination, which results in achievement of a diversity of approximately $10^{20}$. According to the gene amplification method of the present invention, it is possible to analyze such diversified T cell receptor and B cell receptor repertoires.

In order to analyze T cell receptor and B cell receptor repertoires, it is possible to extract and purify total mRNA from T cells of mammals such as humans and mice and amplify the TCR gene by the gene amplification method of the present invention. It is also possible to extract or purify total mRNA from splenocytes or spleen tissue.

Gene amplification can be carried out by the method described in 2 above. In such case, a primer that is specifically annealed with the nucleotide sequence of the C region can be used as a reverse primer. As the C region is a constant region, it has few sequence variations. Therefore, by using one or several types of reverse primers, all T cell receptor genes can be amplified.

In conventional methods (e.g., multiplex PCR) in which a plurality of forward primers and reverse primers specific to a T cell receptor gene are used, a region in the vicinity of the 5' end in the V region cannot be amplified in many cases, thereby making it difficult to carry out sequencing of such portion. According to the gene amplification method of the present invention, an adapter ligated on the 5' end side of the V region end, and a forward primer that binds to the adapter is used. Therefore, it is possible to amplify also the 5' end of the V region or a portion of the L region present on the 5' end side of the V region, thereby making it possible to amplify a 500- to 600-bp region of the entire V region from the J region involved in T cell receptor reconstruction for sequencing.

According to the gene amplification method of the present invention, it is possible to add an adapter to the 5' end of a T cell receptor gene and carry out PCR using an adapter forward primer and a C region-specific primer, thereby making it possible to uniformly amplify all T cell receptor genes.

Repertoire analysis can be conducted by sequencing of the amplification genes. At such time, a next-generation sequencer (second-generation sequencer) may be used, which can carry out sequencing of nucleotide sequences of several tens of millions of DNA fragments in a simultaneous and parallel manner. As such next-generation sequencer, Genome Sequencer FLX (GD FLX) (Roche) or Illumina HiSeq/MiSeq (Illumina) can be used.

This method enables, for example, analysis of T cell receptor repertoire of T cell receptors of a patient affected with a disease and identification of T cell receptors specific to the disease.

When repertoire analysis is carried out by the method of the present invention, the nucleotide sequence match rate is high and not less than 80% of genes with a nucleotide sequence match rate of 90% are present. In other words, specific gene amplification can be properly carried out by the method of the present invention. As a result, it is possible to reflect the proportion of the repertoire of antigen receptors such as an in vivo T cell receptor (TCR) or B cell receptor (BCR).

4. Inhibitory Primer

The present invention also encompasses an inhibitory primer used for unbiased gene amplification in the adapter ligation PCR amplification method.

It is possible to amplify a particular gene without bias using the inhibitory primer of the present invention.

It happens that an adapter is added to both ends of DNA. Therefore, when a primer having no particular sequence, such as the adapter of the present invention described in 1 above, is used as is, PCR amplification takes place in the presence of the adapter portion alone. Therefore, in order to prevent amplification of an antisense strand induced by an adapter portion serving as a primer, an inhibitory primer can be designed so that it comprises the nucleotide sequence of a portion of the adapter. In such case, the sequence of an inhibitory primer, which is a part of the nucleotide sequence of the adapter, is designed to be positioned on the 3' end side of the sequence of a forward primer that is annealed with the adapter, i.e., the target gene side. Alternatively, as a primer used for single-stranded cDNA synthesis, an anchored oligo dT primer, in which an anchor sequence is ligated to the 5' end of an oligo dT primer in the manner described in 2 above, is used so as to design an inhibitory primer that comprises the nucleotide sequence of an anchor sequence portion on the 5' end side of the oligo (dT) portion of the anchored oligo dT. It is possible to inhibit an elongation reaction after the inhibitory primer by adding a modifying group capable of inhibit an elongation reaction upon PCR, such as a phosphate group, an amino group, or dideoxyl NTP, on the 3' end side of inhibitory primer. As a result, a particular gene can be amplified without bias using the inhibitory primer.

Figure 2:
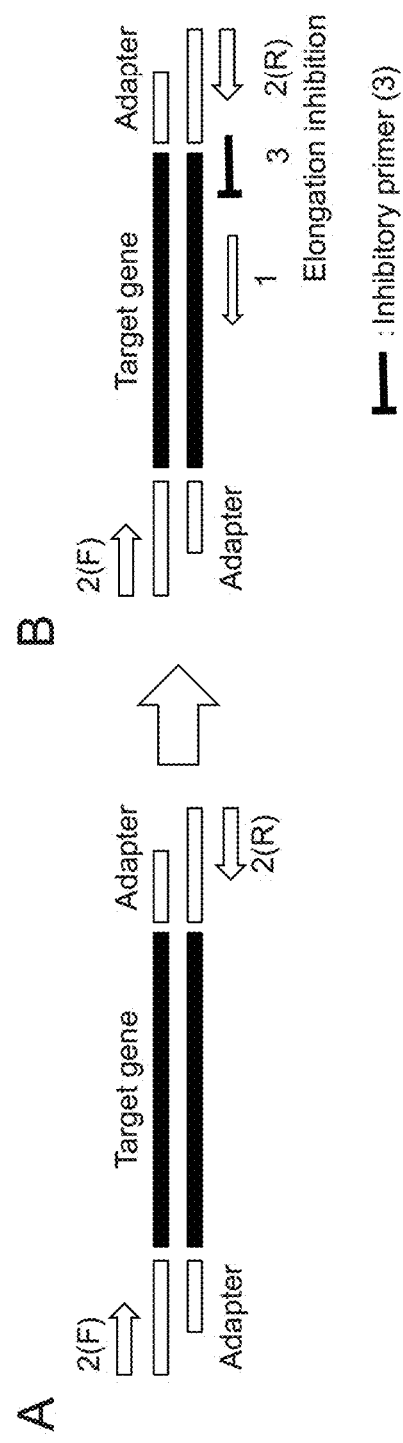
FIG. 2 shows the principle of elongation inhibition with the use of the inhibitory primer of the present invention and the positional relationship of a target gene, an adapter, and a primer.

FIG. 2 illustrates the principle of elongation inhibition with the inhibitory primer of the present invention and the positional relationship of a target gene (double strand shown in black at the center), an adapter, and a primer. In an example shown in FIG. 2, an adapter including no uracil is used as an adapter. FIG. 2A illustrates a case in which no inhibitory primer is used. An adapter binds to both ends of a target gene. A forward primer consisting of a sense strand (long strand) of the adapter is annealed with adapters at both ends of the target gene. Even in a case in which only a forward primer is added as a primer, it happens that elongation is induced by the forward primer in the direction shown with arrow 2 (F). In such case, as shown in FIG. 2A, a sense strand and an antisense strand of an adapter are allowed to have different lengths and a forward primer sequence is determined to be a sequence of a single-stranded portion of a sense strand. Theoretically, a forward primer is not annealed with the adapter and thus elongation does not take place. However, in practice, an antisense strand of an adapter remaining as a free strand that is not bound to a target gene is annealed with a sense strand of an adapter so as to serve as a reverse primer, which might induce elongation from the annealing point in the direction of 2 (R). Further, in a case in which elongation proceeds to an adapter portion so that a strand complementary to the sense strand is formed, the forward primer is annealed with the complementary strand, thereby inducing elongation in the direction of arrow 2 (F). In other words, the elongation reaction is induced by the forward primer alone. FIG. 2B illustrates a case in which an inhibitory primer is used. Reference numeral 1 denotes elongation induced by a target gene-specific reverse primer, reference numeral 2 (F) denotes elongation induced by a forward primer comprising a sequence of a sense strand of an adapter (a long strand of an adapter shown in FIG. 2), and reference numeral 2 (R) denotes elongation when an adapter serves as a reverse primer. Reference numeral 3 denotes the inhibitory primer of the present invention, and elongation in the direction of 2 (R) is inhibited by the inhibitory primer portion. As a result, unless elongation is induced by a reverse primer specific to a target gene, an amplification reaction is not induced by a forward primer alone. An inhibitory primer illustrated in FIG. 2B consists of a sequence of a sense strand of an adapter, and it is modified on the 3' end side. An inhibitory primer includes a portion of an adapter or an anchor sequence portion of an anchored oligo dT primer. Here, an adapter having an antisense strand including uracil as described in 1 above is desirable. However, even in a case in which an adapter including no uracil is used, unbiased amplification is possible because of the function of the inhibitory primer.

When the inhibitory primer of the present invention is used alone, it enables unbiased PCR amplification. The inhibitory primer may be used in combination with the adapter of the present invention described in 1 above. When an adapter including uracil is used, gene amplification proceeds in one direction for elongation as described in 1 above. Meanwhile, even in a case in which an adapter including no uracil is used, it is possible to allow an elongation reaction to proceed in one direction by ligating a modifying group for inhibiting PCR elongation reaction, such as an amino group, to the 3' end of an antisense strand. When it is intended to allow an elongation reaction to proceed in one direction, it is most preferable to use the adapter including uracil described in 1 above. Alternatively, it is also possible to conduct an elongation reaction in one direction by using an adapter including no uracil, in which a modifying group for inhibiting PCR elongation reaction, such as an amino group, is ligated to the 3' end of its antisense strand, and the inhibitory primer of the present invention in combination.

Examples of the inhibitory primer of the present invention include: a primer, in which a phosphate group is bound to the 3' end of a nucleotide consisting of the nucleotide sequence of SEQ ID NO: 18 (TO979); and a primer consisting of a nucleotide sequence located on the 5' end side of an oligo dT portion of an oligo dT primer (TO903 oligo (dT) NotI), to which the anchor sequence having a NotI restriction enzyme site of SEQ ID NO: 1 is ligated.

EXAMPLES

The present invention is specifically described with reference to the Examples below. However, the present invention is not limited to the Examples.

Example 1

Gene-Specific Unbiased Amplification Method Using Adapter 1. cDNA Synthesis from RNA Total RNA (up to 10 µg) was prepared from mouse spleen cells, and first strand synthesis was conducted using an oligo dT primer (TO903) having the following sequence.

```
Oligo dT primer
TO903 oligo (dT) Not1:
                                         (SEQ ID NO: 1)
5'-ataagaatgcggccgctaaactatttttttttttttttttt-3'
```

Reagents used herein are described below.

Total RNA (up to 10 µg), 10 mM dNTP (Invitrogen (trademark)), 50 µM oligo dT primer (TO903), 5× first strand buffer (Invitrogen (trademark)), 0.1 M DTT (Invitrogen (trademark)), RNase out (Invitrogen (trademark), 200 units/µl SuperScript III (Invitrogen (trademark))

These were mixed, and a synthesis reaction was conducted at 50° C. for 60 minutes.

Next, second strand synthesis was conducted. The following reagents were mixed with the above synthesis product, and a synthesis reaction was conducted at 16° C. for 120 minutes.

5× 2nd strand buffer (Invitrogen (trademark)), 10 mM dNTPs (Invitrogen (trademark)), *E. coli* DNA ligase (10 units/µl) (Invitrogen (trademark)), *E. coli* DNA polymerase1 (10 units/µl) (Invitrogen (trademark)), RNase H (2 units/µl) (Invitrogen (trademark))

T4 DNA polymerase (TOYOBO) (1 µl (7 units/µl)) was added to the resulting reaction solution, and a reaction was conducted at 16° C. for 5 minutes so that cDNA was blunt-ended.

2. Adapter Binding Reaction

The following oligo DNA TO1011 and TO995 were synthesized as a sense strand and an antisense strand of an adapter.

```
Adapter
                                         (SEQ ID NO: 2)
TO1011   5'-gcatgtacccatacgatgatca ccggacaggaattcc-3'

(SEQ ID NO: 3)
TO995    5'-(p)gga aUU ccU gUc-NH2-3'
```

The boxed portion of the TO1011 sense strand of SEQ ID NO: 2 is the sequence of a forward primer to be annealed with an adapter. In addition, the TO995 antisense strand sequence of SEQ ID NO: 2 is a strand complementary to the underlined portion of TO01011 of SEQ ID NO: 2, which is shown in Italics. The antisense strand is annealed with the portion so that a double-stranded adapter is formed. In TO995, P denotes binding of a phosphate group, and NH₂ denotes binding of an amino group.

The above TO1011 and TO995 (containing deoxyuracil) oligo DNAs were annealed so that an adapter was prepared. cDNA (1 to 2 μg) synthesized in 1 above and the prepared adapter (20 ng/ml) were allowed to react using DNA ligase at 16° C. for 60 minutes so as to be bound with each other.

3. Unbiased Amplification Using Adapter

The content of cDNA provided with an adapter was adjusted to 25 ng per sample.

The following were mixed to result in a reaction solution. 10× Buffer for KOD Plus Ver.2, 2 mM dNTPs, 25 mM MgSO₄, 5 μM F-primer (TO1022), 5 μM R-primer (TO945), DMSO, KOD Plus (1 unit/μl), UNG (2 units/μl)

The sequences of a forward primer (F-primer) TO1022 and a reverse primer (R-primer) TO945 (MCA195) are shown below. The reverse primer (R-primer) TO945 is annealed with a sequence specific to the C region of a mouse T cell receptor (TCR) α chain.

```
        PCR forward primer
        TO 1022:
                                        (SEQ ID NO: 4)
        5'-gcatgtacccatacgatgatcacc-3'
```

The sequence identification number corresponds to the sequence in the boxed portion of TO1011 shown above. PCR reverse primer (for designing specific primers to be amplified, e.g., mouse TCR alpha and beta chains)

```
        Mouse TCR α chain (mouse TCR c region)
        TO945 (MCA195):
                                        (SEQ ID NO: 5)
        5'-agg tga agc ttg tct ggt tgc tc-3'
```

In this Example, TO945 for the mouse TCR α chain was used as a forward primer, and TO1031 for the mouse TCR β chain strand was also designed.

```
        Mouse TCR β chain (mouse TCR c region)
        TO 1031:
                                        (SEQ ID NO: 6)
        5'-cactgtggacctccttgccattc-3'
```

A mixture of the above was treated at 25° C. for 10 to 30 minutes. As a result, a uracil-glycoside bond was degraded by uracil DNA glycosylase (UNG) at each position of uracils included in the adapter portion TO995. Thus, uracils were removed and alkali-sensitive abasic sites were generated in DNA. Then, as a result of reaction at 95° C. for 2 minutes, each abasic site from which uracil had been removed was degraded, and the TO995 portion serving as the adapter antisense portion was degraded.

Thereafter, a usual PCR reaction was conducted under conditions of 30 cycles of 95° C. for 30 sec, 60° C. for 30 sec, and 68° C. for 60 sec. At such time, DMSO (dimethyl sulfoxide) was added to increase sensitivity to specific amplification using the PCR primers. After the reaction, gel extraction was conducted. Regarding a sample containing few lymphocytes, the further amplified gene was subjected to nested PCR, followed by gel electrophoresis after the reaction.

Figure 3:
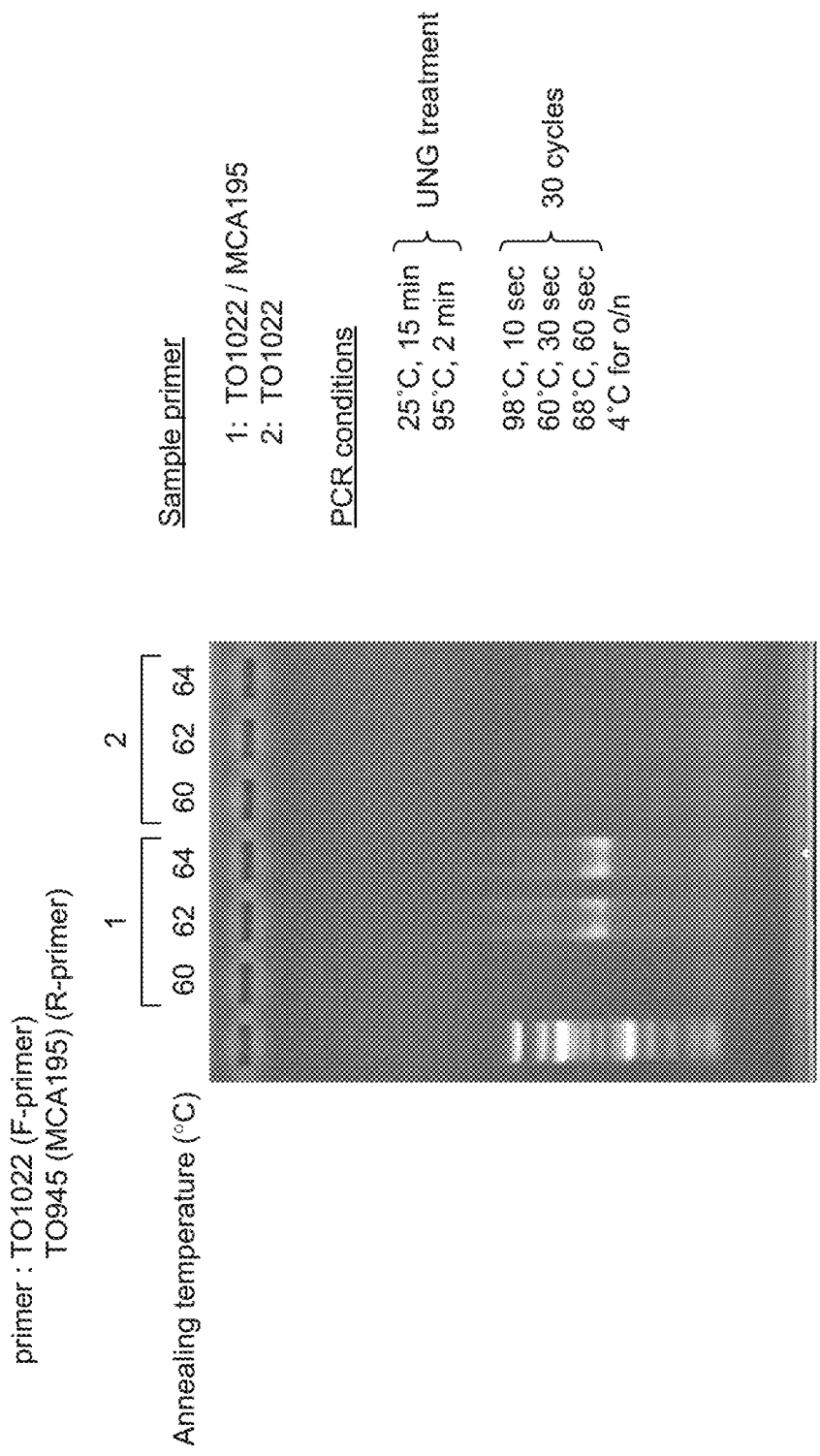
FIG. 3 shows results of gene-specific unbiased amplification using an adapter.

FIG. 3 shows the results. As shown in FIG. 3, gene amplification did not take place using the forward primer alone, while gene amplification took place in the presence of the forward primer and the reverse primer. The results indicate that amplification took place in one direction as shown in FIG. 1.

Example 2

Adapter Sequence Examination

The adapter sequence used in the amplification method in 1 above was examined.

Mouse TCR α chain cDNA (VA18-1) was used as DNA.

An adapter was designed, provided that the base length of a sense strand and that of an antisense strand were the same, the base length was 25 bp or 45 bp, and uracil appeared every 5 bases, 10 bases, or 20 bases.

The sense strand and antisense strand sequences of the adapter used are shown below.

```
25-bp adapter
Original sense strand before insertion of uracil
(GC content: 50%)
                                        (SEQ ID NO: 7)
5'-gcatgtacccatacgatgatcacg-3'
```

Adapter into which uracil was inserted at 5-bp intervals

```
        Adapter GC content: 48%
        Sense strand
                                        (SEQ ID NO: 8)
        5'-gcatctgactgtacgtgatct catg-3'

Antisense strand
                                        (SEQ ID NO: 9)
        5'-(P)CAUGAGAUCA CGUACAGUCA GAUGC-NH₂-3'
```

The boxed portion of the sense strand represents the forward primer sequence.

P denotes binding of a phosphate group, and NH₂ denotes binding of an amino group.

Adapter into which uracil was inserted at 10-bp intervals

```
        Adapter GC content: 48%
        Sense strand
                                        (SEQ ID NO: 8)
        5'-gcatctgactgtacgtgatct catg-3'

Antisense strand
                                        (SEQ ID NO: 10)
        5'-(P)CAUGAGATCA CGUACAGTCA GAUGC-NH₂-3'
```

Adapter into which uracil was inserted at 20-bp intervals

```
        Adapter GC content: 48%
        Sense strand
                                        (SEQ ID NO: 8)
        5'-gcatctgactgtacgtgatct catg-3'

Antisense strand
                                        (SEQ ID NO: 11)
        5'-(P)CAUGAGATCA CGTACAGTCA GAUGC-NH₂-3'
```

45-bp primer

```
Original sense strand before insertion of uracil
(GC content: 51.1%)
                                        (SEQ ID NO: 12)
5'-gcatgtacccatacgatgatcaccggacagaccatgtactacgag-3'
```

Adapter into which uracil was inserted at 5-bp intervals

```
Adapter GC content: 51.1%
Sense strand
                                           (SEQ ID NO: 13)
5'-gcatctgactgtacgtgatct catgtgacctgaccgtagtctacg-3'

Antisense strand
                                           (SEQ ID NO: 14)
5'-(P)CGUAGACUAC GGUCAGGUCA CAUGAGAUCA CGUACAGUCA

GAUGC-NH₂-3'
```

The boxed portion of the sense strand represents the forward primer sequence.

P denotes binding of a phosphate group, and NH₂ denotes binding of an amino group.

Adapter into which uracil was inserted at 10-bp intervals

```
Adapter GC content: 51.1%
Sense strand
                                           (SEQ ID NO: 13)
5'-gcatctgactgtacgtgatct catgtgacctgaccgtagtctacg-3'

Antisense strand
                                           (SEQ ID NO: 15)

5'-(P)CGTAGACUAC GGTCAGGUCA CATGAGAUCA CGTACAGUCA

GATGC-NH₂-3'
```

Adapter into which uracil was inserted at 20-bp intervals

```
Adapter GC content: 51.1%
Sense strand
                                           (SEQ ID NO: 13)
5'-gcatctgactgtacgtgatct catgtgacctgaccgtagtctacg-3'

Antisense strand
                                           (SEQ ID NO: 16)
5'-(P)CGTAGACTAC GGTCAGGUCA CATGAGATCA CGTACAGUCA

GATGC-NH₂-3'
```

The sequences of the forward primer and the reverse primer used for the above adapter are as shown below.

```
Forward primer (TO1168)
                                           (SEQ ID NO: 17)
5'-gcatctgactgtacgtgatc-3'

Reverse primer (TO945 (MCA195)):
Sequence complementary to the C region of mouse
TCR
                                           (SEQ ID NO: 5)
5'-aggtgaagcttgtctggttgctc-3'
```

Gene amplification was conducted by PCR (Pfu) using the above adapters, forward primers, and reverse primers as in the case of Example 1, followed by gel electrophoresis.

Figure 4:
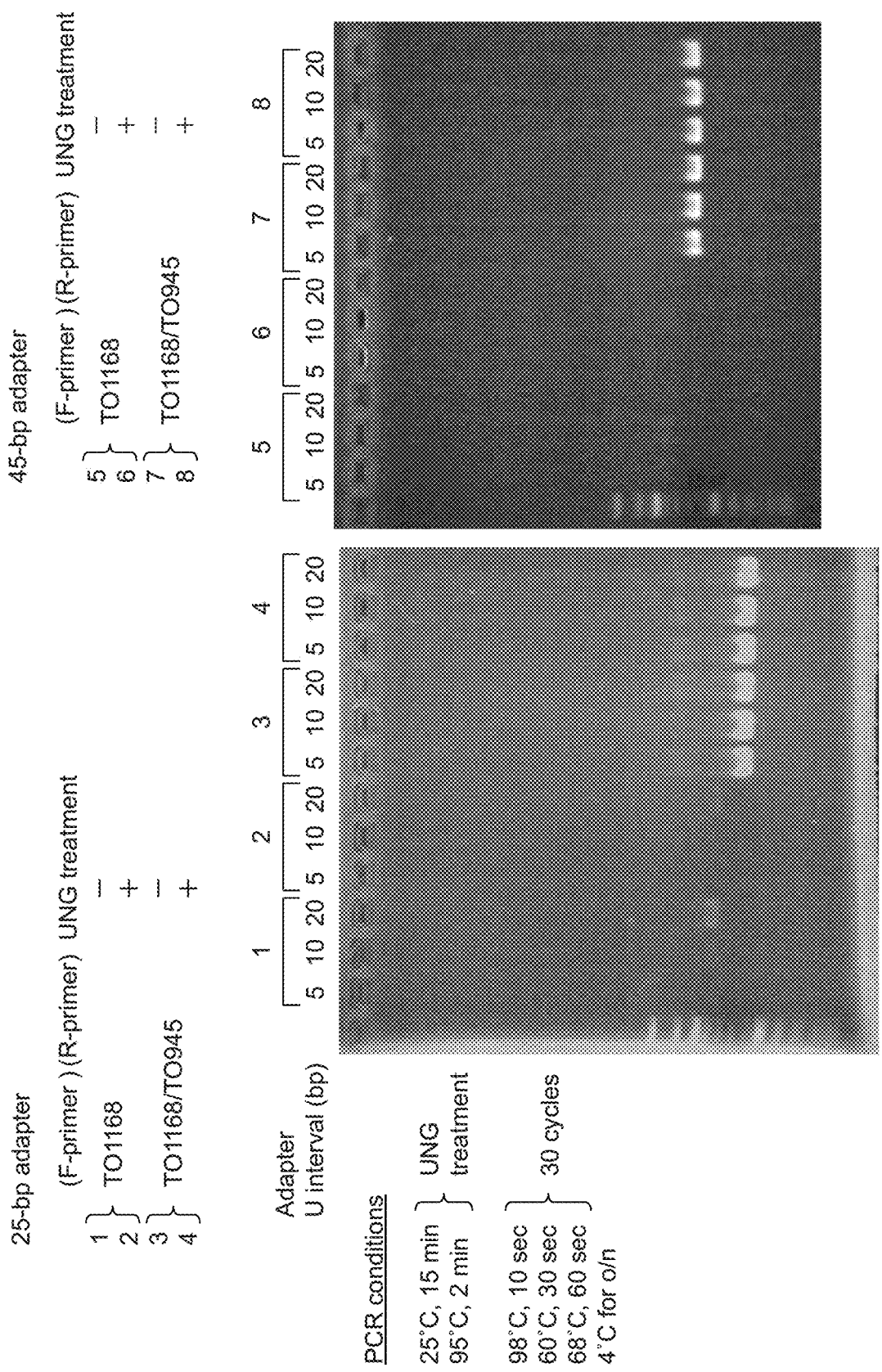
FIG. 4 shows results of examination of adapter sequences.

FIG. 4 shows the results. In FIG. 4, results obtained with or without UNG treatment for a 25-bp adapter in a case in which uracil appeared at 5-bp, 10-bp, or 20-bp intervals and a 45-bp adapter in a case in which uracil appeared at 5-bp, 10-bp, or 20-bp intervals are shown.

As shown in 1 in FIG. 4, when an adapter having a base length of 25 bp was used, amplification took place using the forward primer alone without UNG treatment. As shown in 2 in FIG. 4, when an adapter including uracil present at 5-bp or 10-bp intervals was used, amplification did not take place using the forward primer alone with UNG treatment. Meanwhile, when an adapter including uracil present at 20-bp intervals was used, PCR amplification unexpectedly took place using the forward primer alone.

As shown in 5 and 6 in FIG. 4, when an adapter having a base length of 45 bp was used, amplification took place with the use of the forward primer alone without UNG treatment. In addition, as shown in 6 in FIG. 4, when an adapter including uracil present at 5-bp or 20-bp intervals, PCR amplification did not place with the use of the forward primer alone with UNG treatment. Meanwhile, when an adapter including uracil present at 10-bp intervals was used, PCR amplification unexpectedly took place with the use of the forward primer alone.

The above results revealed that the adapter base length is preferably approximately 25 bp, and it is desirable to insert at least one uracil base at 5-bp intervals.

Example 3

Next-Generation Sequence Analysis

Figure 5:
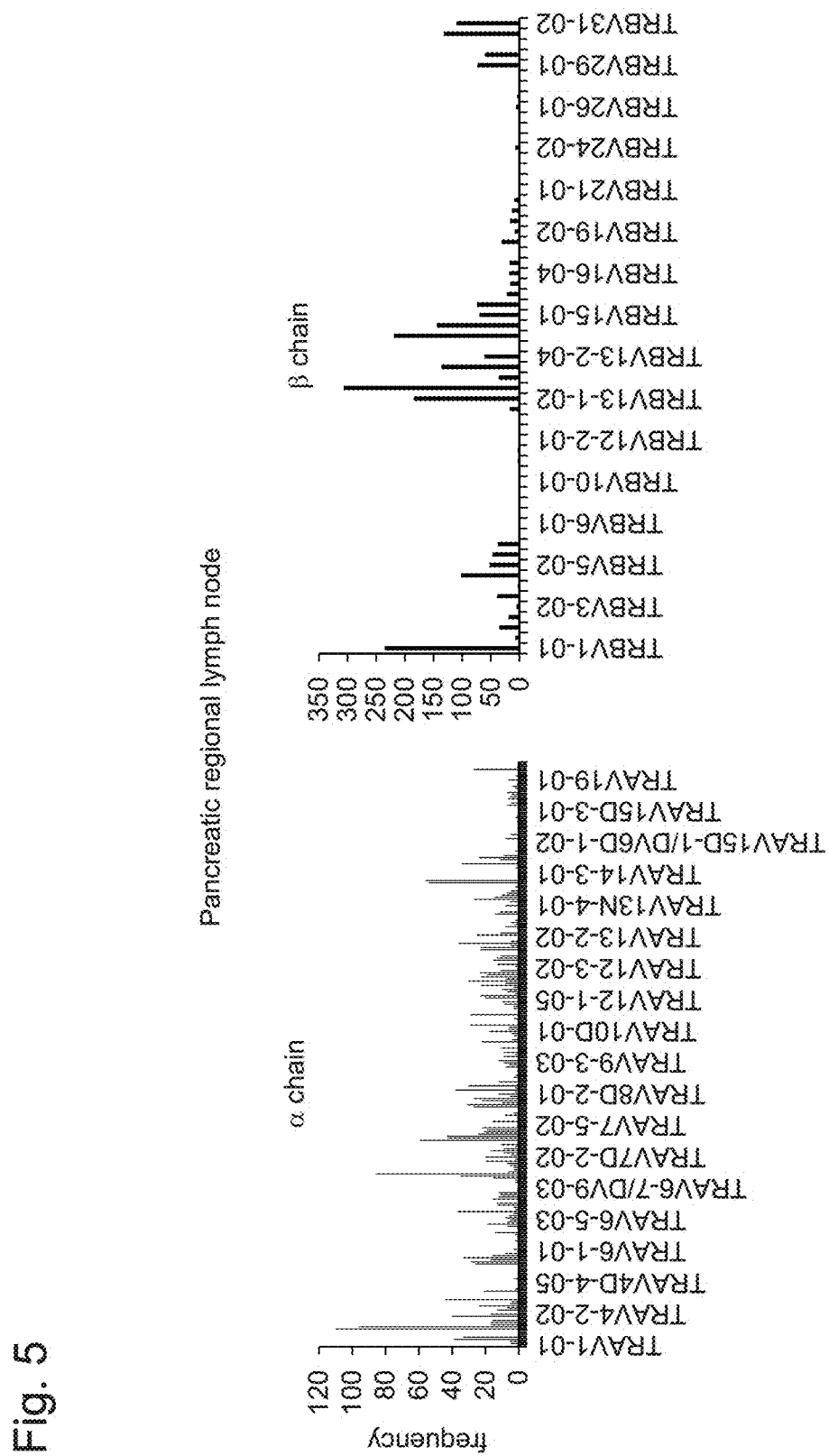
FIG. 5 shows results of comprehensive TCR analysis using a next-generation sequencer.

FIG. 5 shows the results of comprehensive TCR analysis carried out using a next-generation sequencer (Roche 454 GS Junior) by the method described above.

Total RNA was extracted from pancreatic regional lymph nodes of diabetes model mice (NOD mice) and unbiased gene amplification of TCR was carried out by the method described above. The resulting sample was subjected to sequencing using a next-generation sequencer. Frequency of the V strand of each of α and β chains of TCR was analyzed and illustrated.

Example 4

Unbiased Amplification of Inhibitory Primer (Inhibit Primer)

```
Inhibitory primer
TO979:
                                           (SEQ ID NO: 18)
5'-agaatgcggccgctaaactatt(P)-3'
```

(The nucleotide sequence on the 5' end side of the oligo (dT) portion of TO903 oligo (dT) Not1)

```
Adapter sequence
Sense strand TO992:
                                           (SEQ ID NO: 19)
5'-cac atg gat gac gat ca cag gac agg aat tcc-3'

Antisense strand TO994:
                                           (SEQ ID NO: 20)
5'-(P)gga att cct gtc-NH₂-3'

Forward primer (TO993 (AF20N))
TO993:
                                           (SEQ ID NO: 21)
5'-cac atg gat gac gat ca cag-3'

Reverse primer (TO945 (MCA195)):
Sequence complementary to the C region of
mouse TCR
                                           (SEQ ID NO: 22)
5'-aggtgaagcttgtctggttgctc-3'
```

The adapter used in this Example is not an adapter including uracil in its antisense strand, which was used in Example 1. However, an amino group is ligated to the 3' end side of the antisense strand thereof. Although the effects obtained with the use of the adapter including uracil cannot be achieved with the use of such adapter, it is possible to inhibit elongation induced by the forward primer alone through modification with an amino group, thereby allowing elongation in one direction.

The content of cDNA provided with an adapter was adjusted to 25 ng per sample.

The following were mixed to results in a reaction solution. 10× Buffer for KOD Plus Ver. 2, 2 mM dNTPs, 25 mM MgSO$_4$, 5 µM F-primer (TO993), 5 µM R-primer (TO945), DMSO, KOD Plus (1 units/µl), 5 µM Inhibit primer (TO979).

Thereafter, PCR reaction was conducted under conditions of 30 cycles of 95° C. for 30 sec, 60° C. for 30 sec, and 72° C. for 60 sec. After the reaction, gel extraction was conducted. Regarding a sample containing few lymphocytes, the further amplified gene was subjected to nested PCR, followed by gel extraction after the reaction.

Figure 6:
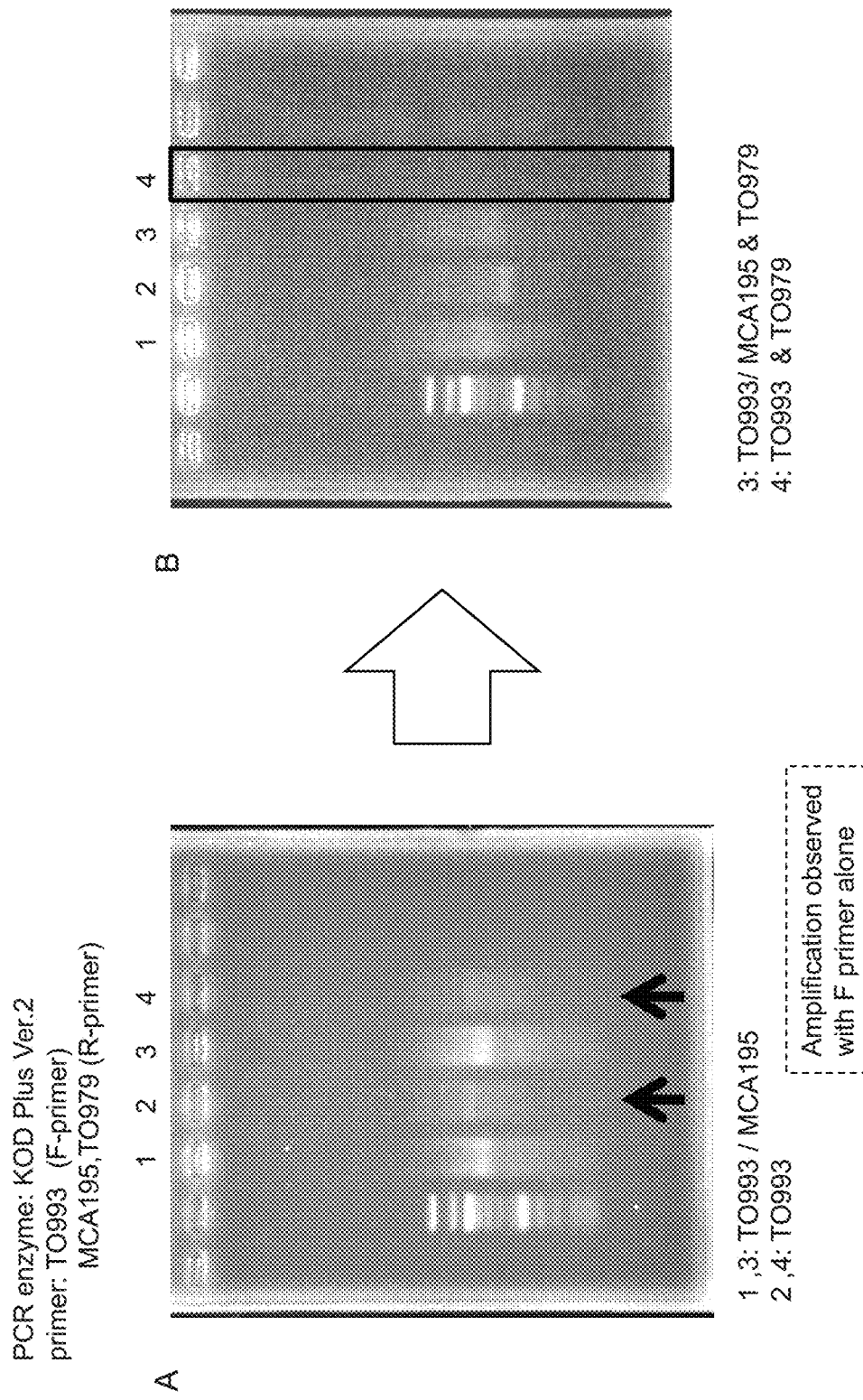
FIG. 6 shows results of unbiased amplification using an inhibitory primer.

FIG. 6 shows the results. Lanes 1 and 3 in FIG. 6A correspond to the addition of the forward primer (TO993) and the reverse primer (MCA195). In such cases, gene amplification was confirmed. Elongation was induced by the reverse primer, and then, elongation was induced by the forward primer. Lanes 2 and 4 correspond to the addition of the forward primer (TO993) alone. In the case of the addition of the forward primer alone, elongation was not induced by the reverse primer (MCA195). In such case, gene amplification usually does not take place. However, the antisense strand of a free remaining adapter functioned as a reverse primer, which unexpectedly caused the forward primer alone to induce elongation. Lane 3 in FIG. 6B corresponds to the addition of the inhibitory primer (TO979) as well as the forward primer (TO993) and the reverse primer (MCA195). In such case, at first, the reverse primer (MCA195) specific to a target gene capable of being annealed on the 3' end side of the inhibitory primer induces elongation even in the presence of the inhibitory primer, which also causes the forward primer (TO993) to induce elongation. Therefore, gene amplification was confirmed. Meanwhile, lane 4 in FIG. 6B corresponds to the addition of the forward primer (TO993) and the inhibitory primer (TO979) only. In such case, even when the antisense strand of a free remaining adapter functions as a reverse primer, elongation is inhibited because the inhibitory primer is annealed on the 3' end side. As a result, the forward primer alone does not induce elongation.

As a result of the use of the inhibitory primer as stated above, gene amplification induced by the forward primer alone was inhibited.

Example 5

Method of Comparing Results of Flow Cytometry Analysis and Results of Next-Generation Sequencer Analysis for TCR Chains 1. Analysis of the Abundance Rate of TCR Chain by Flow Cytometry Lymphocytes were collected from lymph nodes of BALB/c mice. The abundance rate of TCR chain was examined using a fluorescent-labeled antibody. A commercially available fluorescent-labeled antibody (0.25 µg) was added to 1×10$^6$ lymphocytes, followed by staining at 4° C. for 30 minutes. Then, the cells were washed twice with PBS. In addition, in order to label dead cells, the cells were stained with PI (Propidium Iodide). Thus, an analysis sample was obtained. This sample was used for flow cytometry analysis. Flow cytometry analysis was conducted using FACSCanto II (Becton Dickinson).

Fluorescent-labeled antibodies used herein are described below.

Anti-CD4 antibody (clone name: GK1.5)
Anti-CD8 antibody (clone name: 53-6.7)
Anti-Vβ2 antibody (clone name: B20.6)
Anti-Vβ11 antibody (clone name: B20.6)
Anti-Vb8.1.2 antibody (clone name: KJ16-133.18)

In order to calculate abundance rate of specific TCR in T cells, CD4- and CD8-positive cells were designated as T cells. In addition, the number of cells expressing TCR of interest (V β2, Vβ11, Vβ8.1/8.2) among T cells was examined.

As a method of expression frequency calculation, the expression frequency was expressed by the number of TCR-expressing cells of interest/number of T cells×100(%).

The results were determined to be flow cytometry analysis results.

2. Analysis of Abundance Rate of TCR Chain Using Next-Generation Sequencer

Total RNA was extracted from lymph nodes of BALB/c mice and a cDNA library was created by a conventional method. A new-type adapter was provided by the method of the present invention. PCR was carried out by the unbiased gene amplification method for gene amplification of TCR chains. The resulting products were designated as analysis samples. Roche454GS Junior was used as a next-generation sequencer and the samples were analyzed in accordance with the manufacturer's protocol.

Figure 7:
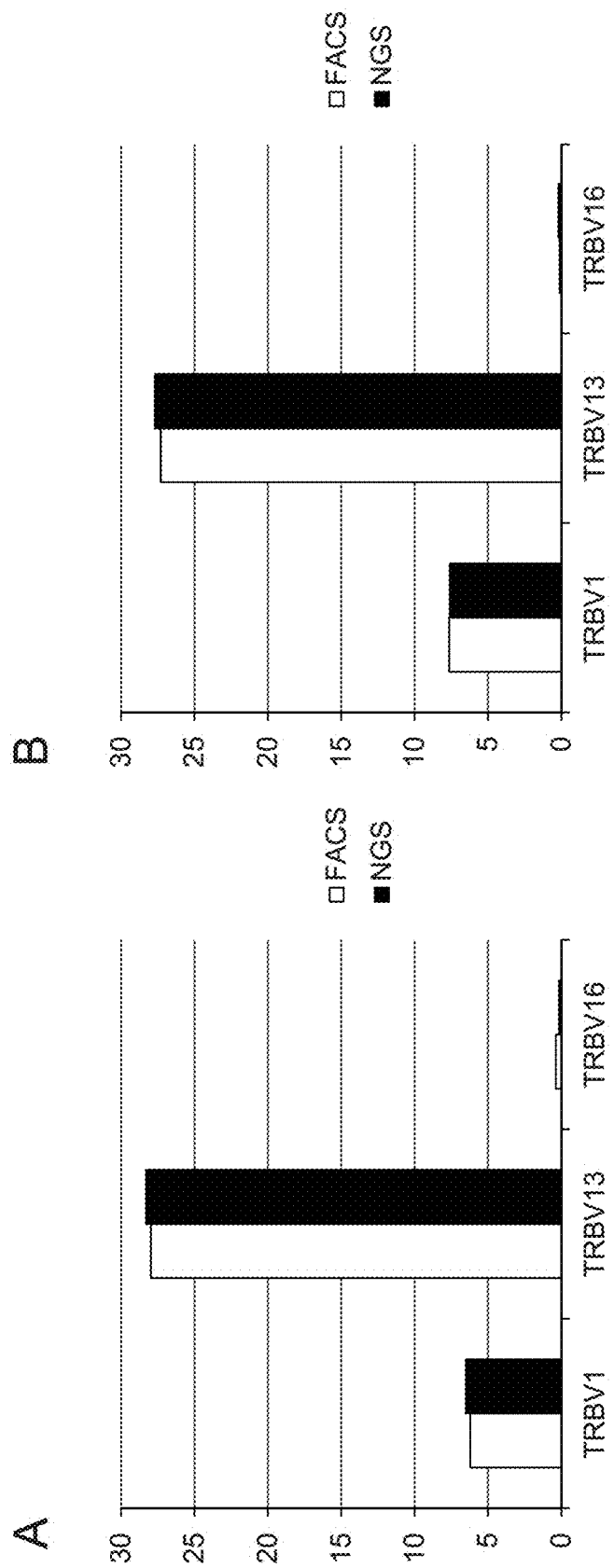
FIG. 7 shows results of comparison of flow cytometry analysis and next-generation sequencer analysis of TCR chains. Two experiments were conducted and the results of the experiments are shown in FIGS. 7A and 7B, respectively.

The obtained results were determined to be the analysis results of the next-generation sequencer and examined and compared with the flow cytometry analysis results. FIG. 7 shows the results. Two experiments were conducted and the results of the experiments are shown in FIGS. 7A and 7B, respectively. In FIG. 7, FACS denotes flow cytometry analysis results, and NGS denotes next-generation sequencer analysis results. As shown in FIG. 7, the next-generation sequencer analysis results are comparable to the FACS analysis results regarding the TCR repertoire expression rate. The results indicate that unbiased gene amplification took place as a result of gene amplification using the double-stranded adapter DNA of the present invention.

The results of this Example indicate accuracy of the method using the adapter of the present invention.

Example 6

Method of Comparative Experimentation of Uniform Amplification of Five Types of Mouse TCRs Having Different Sizes Experimental Method
1. The following mouse TCR cDNA fragments having different sizes (TCR α chain genes each including the C region with a decrease in the length of approximately 50 bp in the descending order) were prepared.
1) 633 bp 25 ng/µl
2) 569 bp 25 ng/µl
3) 517 bp 25 ng/µl
4) 459 bp 25 ng/µl
5) 409 bp 25 ng/µl The five fragments (20 µl each) were mixed to obtain 100 µl of a fragment mix (final concentration of each cDNA: 5 ng/µl).

A conventional adapter (old-type adapter) and the adapter of the present invention (new-type adapter) were separately provided to the fragment mix.
2. A cDNA library of human tissue was prepared, and the old-type adapter and the new-type adapter were separately provided thereto.
3. A human sample provided with the old-type adapter and a human sample provided with the new-type adapter were mixed with a mouse fragment mix provided with old-type adapter and a mouse fragment mix provided with the new-type adapter, respectively, at a concentration ratio of 100:1 (human:mouse=1000 ng:1 ng). Thus, a human and mouse cDNA mix containing the old-type adapter (sample 1) and a human and mouse cDNA mix containing the new-type adapter (sample 2) were prepared. As a result, each fragment mix was unable to be detected as a band.
4. Samples 1 and 2 were separately amplified by the PCR method. For the new-type adapter, PCR was performed after treatment according to the method of the present invention (i.e., after UNG treatment).

PCR conditions for the old-type adapter sample (sample 1) and the new-type adapter sample (sample 2) are described below.
98° C. for 10 sec
64° C. for 30 sec
68° C. for 60 sec
×25 cycles The primer concentration, PCR buffer, and an enzyme (KOD polymerase) were the same as PCR conditions of the present invention.
Adapter Sequence

```
Old-type adapter
Sense:
(TO904: 5'-gacgatgacgaccgaattcc-3' (SEQ ID NO: 23))

Antisense:
(TO932: 5'-ggaattcggtcgtc-3' (SEQ ID NO: 24))
```
PCR primer

```
Primer for the cDNA sample (sample 1) containing old-type
adapter
Forward primer:
(TO904: 5'-gacgatgacgaccgaattcc-3' (SEQ ID NO: 23))

Reverse primer:
Sequence complementary to the C region of mouse TCR
(TO945: 5'-aggtgaagcttgtctggttgctc-3' (SEQ ID NO: 25))

Primer for the cDNA sample containing the new-type adapter
(sample 2)
Forward primer:
(TO1022: 5'-gcatgtacccatacgatgatcacc-3' (SEQ ID NO: 26))

Reverse primer:
Sequence complementary to the C region of mouse TCR
(TO945: 5'-aggtgaagcttgtctggttgctc-3' (SEQ ID NO: 25))
```

5. Samples 1 and 2 were separately amplified by the PCR method and then analyzed by bioanalyzer Agilent 2100 (Agilent Technologies) and the results were illustrated.

Figure 8:
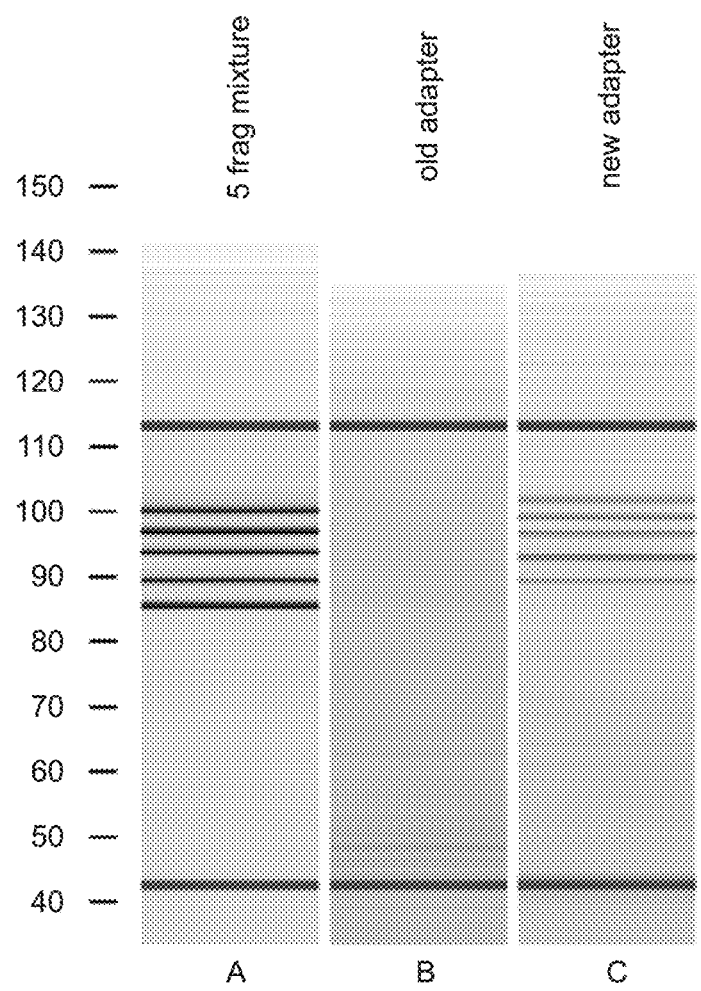
FIG. 8 shows that unbiased amplification of five types of mouse TCRs having different sizes according to the method of the present invention.

FIG. 8 shows the results. In FIG. 8, A indicates the results for a case in which mouse TCRs having five different sizes were uniformly mixed. B indicates the results of the conventional amplification method with the addition of the old-type adapter. C indicates the results of the amplification method of the present invention with the addition of the new-type adapter. As shown in B, no band was confirmed by the conventional amplification method, and non-specific matters were amplified. The results mean that biased gene amplification took place by conventional AL-PCR. Meanwhile, as shown in C, five bands were confirmed in the case of the amplification method of the present invention with the use of the double-stranded adapter DNA of the present invention, indicating that desired amplification of the gene of interest took place and the gene length was elongated by approximately 50 bp, which corresponds to the added adapter portion. Specifically, it was successfully confirmed that unbiased gene amplification took place.

FIG. 9A shows abundance rate of each TCR in a uniform mixture of mouse TCRs having five different sizes before PCR. FIG. 9B shows abundance rate of each TCR after PCR with the use of the adapter of the present invention. It was impossible to determine TCR abundance rate in the case of conventional AL-PCR amplification with the use of the old-type adapter. As shown in FIG. 9, there was substantially no change in abundance rate as a result of PCR amplification with the use of the adapter of the present invention regardless of size differences.

As a result of comparison with the conventional method with the use of a library of a mixture of TCR genes having different sizes, biased amplification results were obtained via non-specific gene amplification for conventional AL-PCR. According to the method of the present invention, gene amplification of interest was achieved, and less biased amplification was achieved regardless of size differences. In the case of the method of the present invention, the resulting abundance rate was substantially the same as the original abundance rate, indicating less biased amplification was achieved.

The results in this Example indicate accuracy of the method with the use of the double-stranded adapter DNA of the present invention.

Example 7

Comparison of Gene Amplification Accuracy Upon TCR Repertoire Analysis

TCRs may be classified into a different repertoire due to a difference of several bases. If gene amplification is correctly carried out, accurate TCR abundance rate can be analyzed. For accurate analysis of TCR abundance rate, it is desirable that the nucleotide sequence match rate be not less than 90%. In this Example, a comparison of gene amplification accuracy upon TCR repertoire analysis was examined.

Method

1. Total RNA was extracted from lymph nodes of BALB/c mice. A cDNA library was created by a conventional method. An old-type adapter sample, to which a conventional adapter (old-type adapter) had been added, and a new-type adapter sample, to which the adapter of the present invention (new-type adapter) had been added, were designated as sample 1 and sample 2, respectively.

2. Samples 1 and 2 were separately amplified by the PCR method. For the new-type adapter, PCR was performed after treatment according to the method of the present invention (i.e., after UNG treatment).

PCR conditions for the old-type adapter sample (sample 1) and the new-type adapter sample (sample 2) are described below.

98° C. for 10 sec
64° C. for 30 sec
68° C. for 60 sec
×30 cycles
Adapter Sequence

```
Old-type adapter
Sense:
(TO904: 5'-gacgatgacgaccgaattcc-3' (SEQ ID NO: 23))

Antisense:
(TO932: 5'-ggaattcggtcgtc-3' (SEQ ID NO: 24))

PCR primer
Primer for the cDNA sample containing old-type
adapter (sample 1)
Forward primer:
(TO904: 5'-gacgatgacgaccgaattcc-3' (SEQ ID NO: 23))

Reverse primer:
Sequence complementary to the C region of mouse TCR
(TO945: 5'-aggtgaagcttgtctggttgctc-3' (SEQ ID NO: 25))

Primer for the cDNA sample containing the new-type
adapter (sample 2)
Forward primer:
(TO1022: 5'-gcatgtacccatacgatgatcacc-3' (SEQ ID NO: 26))

Reverse primer:
Sequence complementary to the C region of mouse TCR
(TO945: 5'-aggtgaagcttgtctggttgctc-3' (SEQ ID NO: 25))
```

3. Gene amplification of the TCR chain was carried out by PCR. The resulting product was designated as an analysis sample. Roche454GS Junior was used as a next-generation sequencer and the sample was analyzed in accordance with the manufacturer's protocol.

4. Comparison of gene amplification accuracy before and after adapter improvement was conducted for the V region.

The V region sequence was checked against the gene sequences of IMGT (the international ImMunoGeneTics information system for immunoglobulins or antibodies; Web site).

For calculation of the match rate, the degree of match of the TCR-V sequence of a sample with the TCR-V region sequence of interest shown by IMGT (100%) was calculated.

*V* region sequence of sample TCR analyzed/Full-length sequence of the *V* region of interest at IMGT×100(%)

Example) In a case in which the full-length sequence of the V region of interest of IMGT is 100 bp, given that 80 bp of the V region of sample TCR analyzed matches the sequence of IMGT, the match rate is 80%.

A distribution of the match rate was calculated as follows.

Number of TCRs with a match rate of ●●%/Total number of TCRs×100(%)

The above match rates were classified from A to F and illustrated.

The match rate falls within the following scope.

A: 0-59%, B: 60-69%, C: 70-79%, D: 80-89%, E: 90-99%, F: 100%

Figure 10:
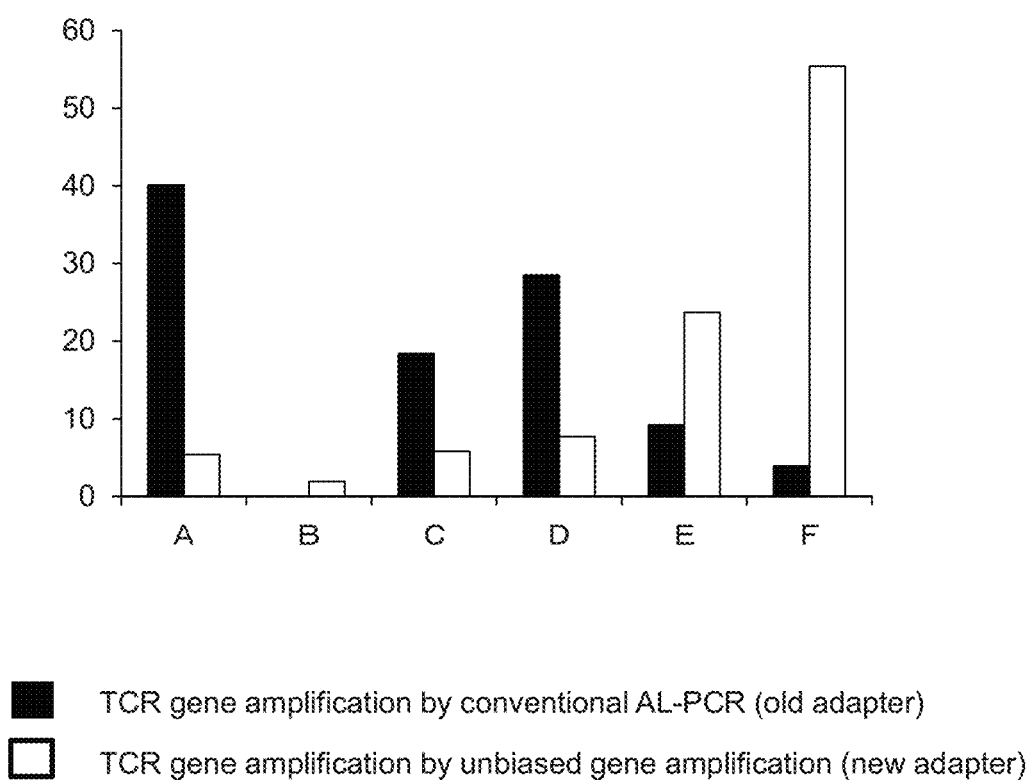
FIG. 10 shows accuracy of gene amplification upon TCR repertoire analysis.

FIG. 10 shows the results. As shown in FIG. 10, as a result of comparison of gene amplification accuracy upon TCR repertoire analysis, in the case of conventional adapter ligation PCR (AL-PCR), the TCR gene match rate was low (black). Meanwhile, in the case of the method of the present invention with the use of the double-stranded adapter DNA of the present invention, the TCR gene match rate was high (genes with a match rate of not less than 90% accounted for not less than 80%), indicating that specific gene amplification took place in a proper manner (white). When the TCR gene match rate increases, errors decrease upon analysis. Thus, it can reflect the in vivo TCR proportion.

The results in this Example indicate accuracy of the method with the use of the double-stranded adapter DNA of the present invention.

INDUSTRIAL APPLICABILITY

According to the gene-specific unbiased amplification method of the present invention, it is possible to conduct comprehensive amplification of genes having various repertoires such as T cell receptor (TCR) or B cell receptor (BCR) repertoires so as to analyze the genes, making it possible to utilize the method for clinical practice, e.g., identification of disease-specific TCRs.

All publications, patents, and patent applications cited herein are incorporated herein by reference in their entirety.

SEQUENCE LISTING

SEQ ID NOS: 1, 4, 5, 6, 17, 18, 21, 22, and 23 to 26 (primers)

SEQ ID NOS: 2, 3, 7 to 16, 19, and 20 (synthesis)

The invention claimed is:

1. A double stranded adapter DNA, which is used for unbiased gene amplification and has the following features:
   (a) the double-stranded adapter DNA has a sense strand and an antisense strand that are annealed with each other, the base length of the sense strand being equal to or longer than the base length of the antisense strand;
   (b) the base length of the sense strand is 15 to 40 bp;
   (c) the antisense strand includes a plurality of uracil bases and the number of uracil bases included in the antisense strand accounts for 10% to 25% of the number of bases of the antisense strand, and uracil is present every 5 to 10 bases;
   (d) one end of the adapter DNA is in the form of a blunt end;
   (e) the other end of the adapter DNA binds to a target gene to be amplified;
   (f) a part or all of the sense strand corresponds to a forward primer sequence used for gene amplification; and
   (g) a phosphate group is bound to the 5' end of the antisense strand strand and an amino group is bound to the 3' end of the antisense strand;
   (h) the CG content of the adapter DNA is 45% to 55%.

2. An unbiased gene amplification kit, which includes the double-stranded adapter DNA according to claim 1, and a primer comprising a part or all of a sequence of the sense strand of the double-stranded adapter DNA.

3. An unbiased gene amplification kit, which includes the double-stranded adapter DNA according to claim 1, a primer comprising a part or all of a sequence of the sense strand of the double-stranded adapter DNA, and an inhibitory primer having a sequence comprising:
   (i) all or a part of a sequence of an anchor sequence portion of an anchored oligo dT primer in which an anchor sequence is ligated to the 5' end of an oligo dT primer, the anchored oligo dT primer being used when synthesizing single-stranded cDNA from mRNA of a target gene to be amplified; or
   (ii) a partial sequence of the sense strand of the double-stranded adapter DNA, and
the inhibitory primer is modified with a phosphate group, an amino group, or dideoxyl NTP on its 3' end side.

* * * * *

SEQUENCE LISTING

<160> NUMBER OF SEQ ID NOS: 26

<210> SEQ ID NO 1
<211> LENGTH: 41
<212> TYPE: DNA
<213> ORGANISM: Artificial
<220> FEATURE:
<223> OTHER INFORMATION: Primer

<400> SEQUENCE: 1
ataagaatgc ggccgctaaa ctattttttt ttttttttt t         41

<210> SEQ ID NO 2
<211> LENGTH: 37
<212> TYPE: DNA
<213> ORGANISM: Artificial
<220> FEATURE:
<223> OTHER INFORMATION: Synthetic

<400> SEQUENCE: 2
gcatgtaccc atacgatgat caccggacag gaattcc         37

<210> SEQ ID NO 3
<211> LENGTH: 12
<212> TYPE: DNA
<213> ORGANISM: Artificial
<220> FEATURE:
<223> OTHER INFORMATION: Synthetic

<400> SEQUENCE: 3
ggaauuccug uc         12

<210> SEQ ID NO 4
<211> LENGTH: 24
<212> TYPE: DNA
<213> ORGANISM: Artificial
<220> FEATURE:
<223> OTHER INFORMATION: Primer

<400> SEQUENCE: 4
gcatgtaccc atacgatgat cacc         24

<210> SEQ ID NO 5
<211> LENGTH: 23
<212> TYPE: DNA
<213> ORGANISM: Artificial
<220> FEATURE:
<223> OTHER INFORMATION: Primer

<400> SEQUENCE: 5
aggtgaagct tgtctggttg ctc         23

<210> SEQ ID NO 6
<211> LENGTH: 23
<212> TYPE: DNA
<213> ORGANISM: Artificial
<220> FEATURE:
<223> OTHER INFORMATION: Primer

<400> SEQUENCE: 6
cactgtggac ctccttgcca ttc         23

<210> SEQ ID NO 7
<211> LENGTH: 24
<212> TYPE: DNA
<213> ORGANISM: Artificial

<220> FEATURE:
<223> OTHER INFORMATION: Synthetic

<400> SEQUENCE: 7
gcatgtaccc atacgatgat cacg                                                        24

<210> SEQ ID NO 8
<211> LENGTH: 25
<212> TYPE: DNA
<213> ORGANISM: Artificial
<220> FEATURE:
<223> OTHER INFORMATION: Synthetic

<400> SEQUENCE: 8
gcatctgact gtacgtgatc tcatg                                                       25

<210> SEQ ID NO 9
<211> LENGTH: 25
<212> TYPE: DNA
<213> ORGANISM: Artificial
<220> FEATURE:
<223> OTHER INFORMATION: Synthetic

<400> SEQUENCE: 9
caugagauca cguacaguca gaugc                                                       25

<210> SEQ ID NO 10
<211> LENGTH: 25
<212> TYPE: DNA
<213> ORGANISM: Artificial
<220> FEATURE:
<223> OTHER INFORMATION: Synthetic

<400> SEQUENCE: 10
caugagatca cguacagtca gaugc                                                       25

<210> SEQ ID NO 11
<211> LENGTH: 25
<212> TYPE: DNA
<213> ORGANISM: Artificial
<220> FEATURE:
<223> OTHER INFORMATION: Synthetic

<400> SEQUENCE: 11
caugagatca cgtacagtca gaugc                                                       25

<210> SEQ ID NO 12
<211> LENGTH: 45
<212> TYPE: DNA
<213> ORGANISM: Artificial
<220> FEATURE:
<223> OTHER INFORMATION: Synthetic

<400> SEQUENCE: 12
gcatgtaccc atacgatgat caccggacag accatgtact acgag                                 45

<210> SEQ ID NO 13
<211> LENGTH: 45
<212> TYPE: DNA
<213> ORGANISM: Artificial
<220> FEATURE:
<223> OTHER INFORMATION: Synthetic

<400> SEQUENCE: 13
gcatctgact gtacgtgatc tcatgtgacc tgaccgtagt ctacg                                 45

-continued

```
<210> SEQ ID NO 14
<211> LENGTH: 45
<212> TYPE: DNA
<213> ORGANISM: Artificial
<220> FEATURE:
<223> OTHER INFORMATION: Synthetic

<400> SEQUENCE: 14
cguagacuac ggucagguca caugagauca cguacaguca gaugc            45

<210> SEQ ID NO 15
<211> LENGTH: 45
<212> TYPE: DNA
<213> ORGANISM: Artificial
<220> FEATURE:
<223> OTHER INFORMATION: Synthetic

<400> SEQUENCE: 15
cgtagacuac ggtcagguca catgagauca cgtacaguca gatgc            45

<210> SEQ ID NO 16
<211> LENGTH: 45
<212> TYPE: DNA
<213> ORGANISM: Artificial
<220> FEATURE:
<223> OTHER INFORMATION: Synthetic

<400> SEQUENCE: 16
cgtagactac ggtcagguca catgagatca cgtacaguca gatgc            45

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
gcatctgact gtacgtgatc                                        20

<210> SEQ ID NO 18
<211> LENGTH: 22
<212> TYPE: DNA
<213> ORGANISM: Artificial
<220> FEATURE:
<223> OTHER INFORMATION: Primer

<400> SEQUENCE: 18
agaatgcggc cgctaaacta tt                                     22

<210> SEQ ID NO 19
<211> LENGTH: 32
<212> TYPE: DNA
<213> ORGANISM: Artificial
<220> FEATURE:
<223> OTHER INFORMATION: Synthetic

<400> SEQUENCE: 19
cacatggatg acgatcacag gacaggaatt cc                          32

<210> SEQ ID NO 20
<211> LENGTH: 12
<212> TYPE: DNA
<213> ORGANISM: Artificial
<220> FEATURE:
<223> OTHER INFORMATION: Synthetic
```

```
<400> SEQUENCE: 20
ggaattcctg tc                                                       12

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
cacatggatg acgatcacag                                               20

<210> SEQ ID NO 22
<211> LENGTH: 23
<212> TYPE: DNA
<213> ORGANISM: Artificial
<220> FEATURE:
<223> OTHER INFORMATION: Primer

<400> SEQUENCE: 22
aggtgaagct tgtctggttg ctc                                           23

<210> SEQ ID NO 23
<211> LENGTH: 20
<212> TYPE: DNA
<213> ORGANISM: Artificial
<220> FEATURE:
<223> OTHER INFORMATION: Primer

<400> SEQUENCE: 23
gacgatgacg accgaattcc                                               20

<210> SEQ ID NO 24
<211> LENGTH: 14
<212> TYPE: DNA
<213> ORGANISM: Artificial
<220> FEATURE:
<223> OTHER INFORMATION: Primer

<400> SEQUENCE: 24
ggaattcggt cgtc                                                     14

<210> SEQ ID NO 25
<211> LENGTH: 23
<212> TYPE: DNA
<213> ORGANISM: Artificial
<220> FEATURE:
<223> OTHER INFORMATION: Primer

<400> SEQUENCE: 25
aggtgaagct tgtctggttg ctc                                           23

<210> SEQ ID NO 26
<211> LENGTH: 24
<212> TYPE: DNA
<213> ORGANISM: Artificial
<220> FEATURE:
<223> OTHER INFORMATION: Primer

<400> SEQUENCE: 26
gcatgtaccc atacgatgat cacc                                          24
```